US 6,641,393 B2

United States Patent
Trichas

(10) Patent No.: US 6,641,393 B2
(45) Date of Patent: Nov. 4, 2003

(54) DENTAL TRAY AND MIXING TIP ASSEMBLY

(75) Inventor: Konstantine Trichas, Basking Ridge, NJ (US)

(73) Assignee: Tri Del, LLC, New York, NY (US)

( * ) Notice: Subject to any disclaimer, the term of this patent is extended or adjusted under 35 U.S.C. 154(b) by 103 days.

(21) Appl. No.: 10/224,461

(22) Filed: Aug. 21, 2002

(65) Prior Publication Data

US 2003/0044747 A1 Mar. 6, 2003

Related U.S. Application Data

(63) Continuation-in-part of application No. 09/943,402, filed on Aug. 31, 2001, now abandoned.

(51) Int. Cl.[7] .................................................. A61C 9/00
(52) U.S. Cl. .......................................... 433/37; 433/89
(58) Field of Search ............................. 433/36, 37, 80, 433/89, 90

(56) References Cited

U.S. PATENT DOCUMENTS

| 2,155,334 A | * | 4/1939 | Sitkin et al. | |
| 2,452,903 A | * | 11/1948 | Coffey | |
| 2,458,145 A | * | 1/1949 | Coffey | |
| 3,722,097 A | * | 3/1973 | Colman et al. | |
| 4,378,211 A | * | 3/1983 | Lococo | 433/36 |
| 4,382,785 A | * | 5/1983 | Lococo | 433/36 |
| 5,104,315 A | * | 4/1992 | McKinley | 433/80 |
| 5,370,533 A | * | 12/1994 | Bushnell | 433/36 |
| 5,636,985 A | * | 6/1997 | Simmen et al. | 433/37 |
| 5,890,894 A | * | 4/1999 | Mio et al. | 433/37 |

* cited by examiner

Primary Examiner—Ralph A. Lewis
(74) Attorney, Agent, or Firm—Dan M. de la Rosa

(57) ABSTRACT

A dental tray and mixing tip assembly with a material delivery system is provided, the tray comprises at least one material retention surface; and a rapid flow delivery device, the device comprises a channel having an inlet and at least one outlet, the channel and the retention surface being situated on a horizontal plane, the channel being designed to deliver material from the inlet through the outlet and onto the retention surface and a mixing tip comprising a mixing tube having an entrance and an exit; a mixing device, situated within the tube, and the exit of the tip being connected to the inlet of the tray.

18 Claims, 6 Drawing Sheets

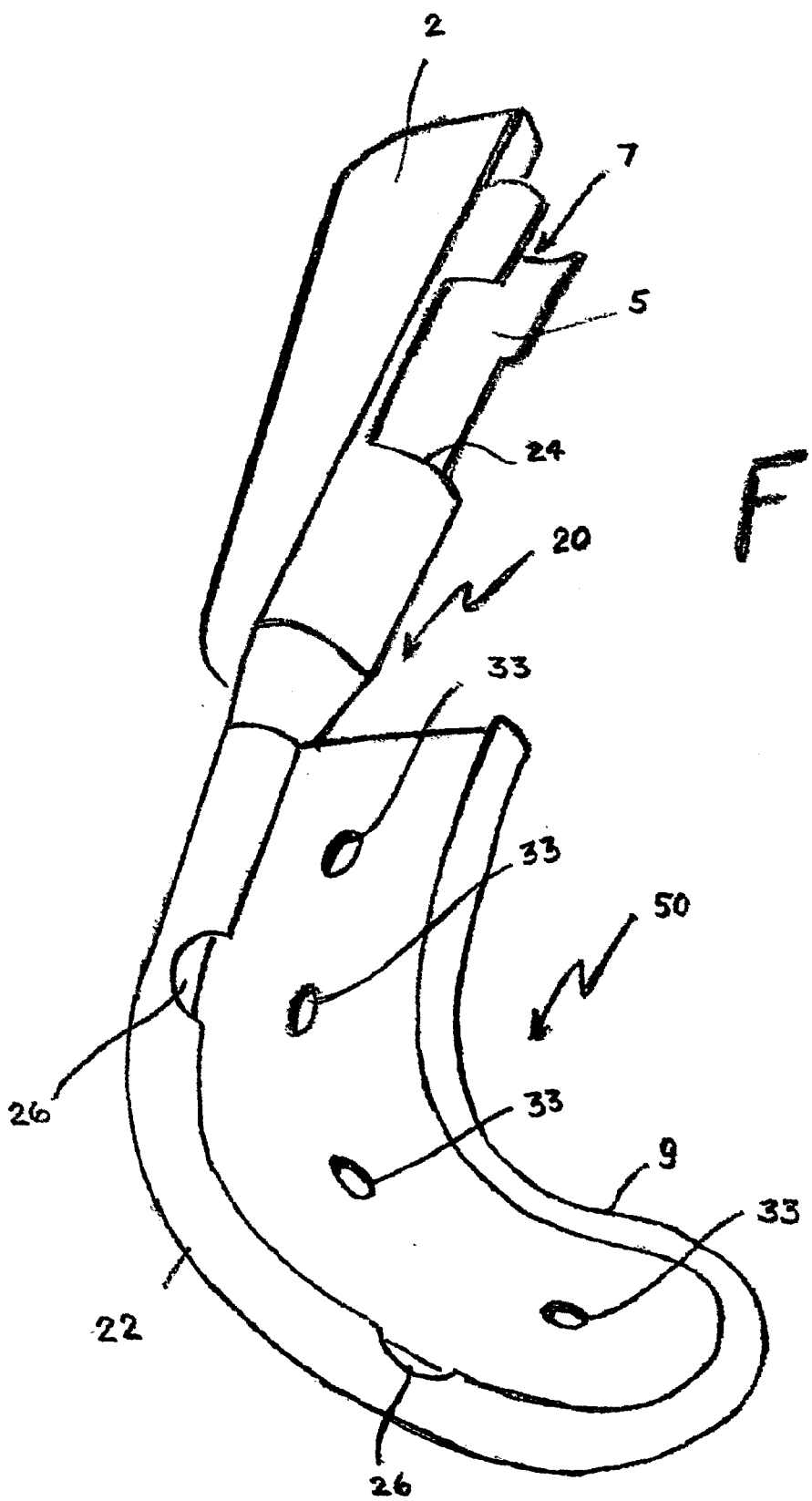

DENTAL TRAY AND MIXING TIP ASSEMBLY

RELATED APPLICATION

This application is a continuation-in-part application of U.S. application Ser. No. 09/943,402, now abandoned, entitled "Dental Tray With Rapid Flow Delivery System" which was filed on Aug. 31, 2001.

BACKGROUND OF THE INVENTION

1. Field of the Invention

This invention relates to a dental tray with a rapid flow delivery system. More specifically, the present invention relates to a tray having a material retention surface and a delivery system comprising a channel being situated parallel to the surface, the channel having an inlet and an outlet designed to deliver the material to the surface. The present invention also relates to a dental tray and mixing tip assembly. And more specifically, the assembly comprises a dental tray having a material retention surface surrounded by peripheral walls and a channel situated within the walls and having an inlet and an outlet; and the tip comprising a mixing tube with an entrance and an exit and a mixing device situated within the tube; and whereby the exit of the tip is connected to the inlet of the dental tray.

2. Description of the Related Art

Dental impressions are a critical aspect of the success of dental prosthesis. The triple tray or closed bite impression is arguably one of the most efficient ways for dentist to make impression and bite registrations of their patients' teeth. Most impressions are taken using two viscosities of impression materials simultaneously; a heavy bodied material such as thixotropic polysiloxane, which is placed onto the impression tray and a flowable hydrophilic material, which is injected onto the patient's teeth. Upon insertion of the tray into the patient's mouth, the patient is instructed to bite down onto the heavy bodied material on the tray to thereby register an impression.

The trays that are present in the market today are single or double arch trays, which require the dentist and/or dental assistant to dispense impression material onto the tray face. In the case of double arch trays, there is a requirement for application of the impression material on both sides of the tray face of the tray. Most trays require at least two individuals to perform these tedious and time sensitive activities to prepare the trays for use with a patient. The trays of today are manually loaded with the impression material. There are no trays in the market that interface with standard mixing tips to expedite this process of loading trays with impression material. There are no trays in the market that have an effective delivery system for loading the impression materials onto the tray face of the trays. In addition, there are no dental tray and mixing tip assemblies that simplify the loading process of impression materials. Furthermore, there are no mixing tips that have a moveable or rotatable mixing device situated within the mixing tube of the mixing tip.

SUMMARY OF THE INVENTION

In one embodiment, the present invention relates to a dental tray comprising a material retention surface, and a rapid flow delivery device, the device comprises a channel having an inlet and an outlet, the channel and the retention surface being situated on a horizontal plane, the channel being designed to deliver material from the inlet through the outlet and onto the retention surface. In another embodiment, the channel of the tray is parallel to the retention surface. In still another embodiment, the channel of the tray is perpendicular to the retention surface. In yet another embodiment, the outlet of said channel is parallel to said retention surface. In still yet another embodiment, the outlet of the channel of the tray is perpendicular to the retention surface.

In a further embodiment, the tray further comprises peripheral walls surrounding the retention surface. In still a further embodiment, the peripheral walls define the retention surface and the delivery device is incorporated within the peripheral walls. In still yet a further embodiment, the tray further comprising a handle, the handle being connected to the delivery device. In still another further embodiment, the circumference of the channel adjacent to the inlet is greater than the circumference of the channel adjacent to the outlet.

In yet another further embodiment, the material for the retention surface includes, but is not limited to, dental impression material, whitening agents, fluoride, dental casting material and mixtures thereof For purposes of this invention, the tray can be used as dental impression trays, denture casting or impression trays, delivery dental trays for whitening agents, cleaning agents, fluoride, etc. The tray and delivery system of the present invention can be used as single or triple trays, full arches, anterior, posterior and quadrant trays.

In another embodiment, the present invention relates to a dental tray comprising: a material retention surface and a rapid flow delivery device; the device comprises a channel having an inlet and an outlet, a portion of the channel being positioned above the retention surface, the channel being designed to deliver material from the inlet through the outlet and onto the retention surface. In still another embodiment, outlet of the channel is positioned above the retention surface of the tray. In yet another embodiment, the peripheral walls surround and define the retention surface and the delivery device is incorporated within the peripheral walls. In still yet another embodiment, the circumference of the channel adjacent to the inlet is greater than the circumference of the channel adjacent to the outlet. In a further embodiment, the tray further comprises a connector situated between the channel and the retention surface. In still a further embodiment, the connector is an elbow connection. In yet a further embodiment, the material includes, but is not limited to dental impression material, whitening agents, fluoride, dental casting material and mixtures thereof.

In another embodiment, the present invention relates to a dental tray comprising: a mouthpiece having an upper and lower portion, the upper portion having an upper material retention surface, the lower portion having a lower material retention surface; and a rapid flow delivery device, the device comprising a channel having an inlet and an outlet, the channel and the mouthpiece being situated on a horizontal plane, the channel being designed to deliver material from the inlet through the outlet and onto both the upper and lower retention surfaces. In still another embodiment, the inlet of the channel bisects the mouthpiece of the tray. In still yet another embodiment, the tray further comprises peripheral walls surrounding the mouthpiece. In a further embodiment, the peripheral walls define the mouthpiece and the delivery device is incorporated within the peripheral walls. In still a further embodiment, the circumference of the channel adjacent to the inlet is greater than the circumference of the channel adjacent to the outlet.

In yet a further embodiment, the present invention relates to a method of manufacturing a dental tray, the method comprising: providing a mouthpiece having an upper and lower portion, the upper portion having an upper material retention surface, the lower portion having a lower material retention surface; and providing a rapid flow delivery device, the device comprising a channel having an inlet and an outlet, the channel and the mouthpiece being situated on a horizontal plane, the channel being designed to deliver material from the inlet through the outlet and onto both the upper and lower retention surfaces. In still yet a further embodiment, the method further comprises providing peripheral walls for surrounding the retention surface and incorporating the delivery device within the peripheral walls. In another further embodiment, the channel is situated parallel to the mouthpiece of the tray. In still another further embodiment, the channel is situated perpendicular to the mouthpiece of the tray. In yet a further embodiment, a portion of the channel is situated above the mouthpiece of the tray.

In another embodiment, the present invention relates to a dental tray and mixing tip assembly comprising: a tray comprising at least one material retention surface and peripheral walls surrounding at least a portion of the retention surface; and a rapid flow delivery device, the device comprising a channel having an inlet and at least one outlet, a portion of the channel being positioned above the retention surface, the channel being designed to deliver material from the inlet through the outlet and onto the retention surface, the delivery device being incorporated within the peripheral walls; and a mixing tip comprising a mixing tube having an entrance and an exit; a mixing device situated within the tube, and the exit of the tip being connected to the inlet of the channel of the delivery device of the tray. For purposes of this invention, the mixing tip of the present invention can apply to any and all mixing tips in the market. The mixing device can apply to stationary and moveable devices for mixing the separate fluids within the mixing tip as the fluid travels through the tip and the mixed fluids enter the delivery device and end up on the retention surfaces of the dental tray.

In a further embodiment, the channel in the tray of the assembly of the present invention is parallel to the retention surface. In still another embodiment, the outlet of the channel is parallel to the retention surface. In yet another embodiment, the outlet of the channel is parallel to the retention surface.

In still yet another embodiment, the mixing device is rotatable within the mixing tube, whereby a pressure created by the flow of at least two separate fluids entering the entrance of the tube causes the mixing device to rotate and thereby mix the fluids. The mixing device can be twisted ribbon. In still a further embodiment, the tip further comprises a means for preventing the back flow of the fluids to be mixed and thereby preventing the fluids from exiting the entrance of the tip.

In another embodiment, the present invention relates to a dental tray and mixing tip assembly comprising: a mouthpiece having an upper and lower portion, the upper portion having an upper material retention surface, the lower portion having a lower material retention surface and the mouthpiece further comprising peripheral walls; and a rapid flow delivery device, the device comprising a channel having an inlet and at least one outlet, the channel being situated on a horizontal plane with the upper retention surface and being situated above the lower retention surface, the channel being designed to deliver material from the inlet through the outlet and onto both the upper and lower retention surfaces, the channel being situated within the peripheral walls of the mouthpiece; and a mixing tip for receiving and mixing at least two separate fluids, the tip comprising a mixing tube having an entrance and an exit; a means for mixing the fluids, the mixing means being situated within the tube, and the exit of the tip being connected to the inlet of the channel of the delivery device of the tray.

In another further embodiment, the mixing device is moveable within the mixing tube, whereby a pressure created by the flow of at least two separate fluids entering the entrance of the tube causes the mixing device to move and thereby mix the fluids. In another embodiment, the mixing means comprises twisted ribbon. In yet another further embodiment, the tip further comprises a means for preventing the back flow of the fluids to be mixed and thereby preventing the fluids from exiting the entrance of the tip. In another embodiment, the back flow means can be clips, pinchers, and closeable devices for closing the entrance of the mixing when the assembly is removed from the mixing dispenser or gun.

In another embodiment, the assembly of the present invention to any convention mixing dispenser or gun and the pressure of the gun allows the separate fluids to be mixed to enter the entrance of the mixing tip and to be mixed within the tube by the mixing means and then the mixed fluids enter the inlet of the delivery device and then exits the outlet of the delivery device and is transferred onto the contact retention surface of the dental tray whereby it is now ready for insertion into a patient's mouth. In a further embodiment, the mixing means of the present invention is moveable or rotatable within the mixing tube during the mixing process of the fluids while they travel through the mixing tip. In one embodiment, the mixing tip is parallel to the delivery device of the tray. In another embodiment, the mixing tip is perpendicular to the delivery device of the tray. In a further embodiment, the orientation and angles of the mixing tip in relation to the delivery device of the tray has no restriction so long as the tray can fit within a patient mouth and the tip does not inhibit the impression or registration process. In still a further embodiment, the tip is breakable from the tray. In yet a further embodiment, the mixing tip functions as a handle during the impression or registration process. The present invention also relates to a mixing tip with a moveable or rotatable mixing device or mixing means situated within the tube of the mixing tip.

BRIEF DESCRIPTION OF THE DRAWINGS

The accompanying drawings are included to provide a further understanding of the present invention. These drawings are incorporated in and constitute a part of this specification, illustrate done or more embodiments of the present invention, and together with the description, serve to explain the principles of the present invention.

FIG. 8 is a top plan view of another embodiment of the present invention, in particular, a quadrant triple tray with multiple inlets.

Figure 1:
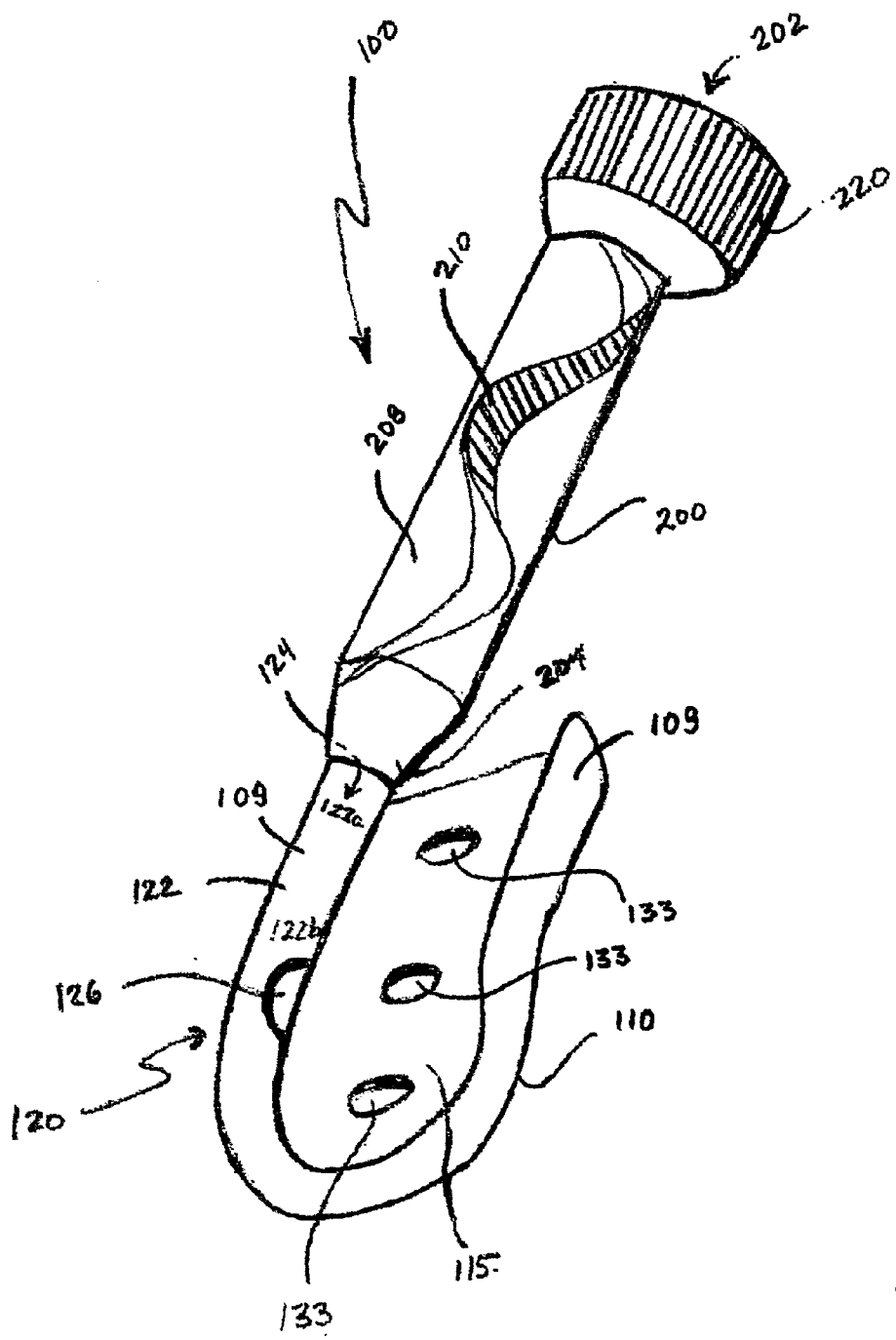
FIG. 1 is a perspective view of one of the embodiments of the dental tray and mixing tip assembly of the present invention, in particular, a single quadrant tray.
Figure 2:
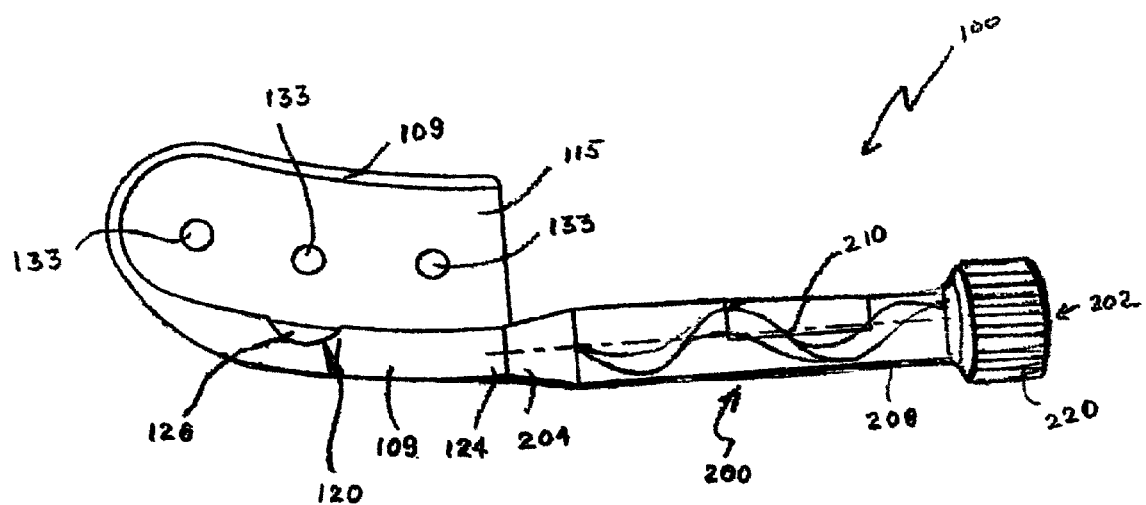
FIG. 2 is an overhead view of the dental tray and tip assembly embodiment shown in FIG. 1.
Figure 3:
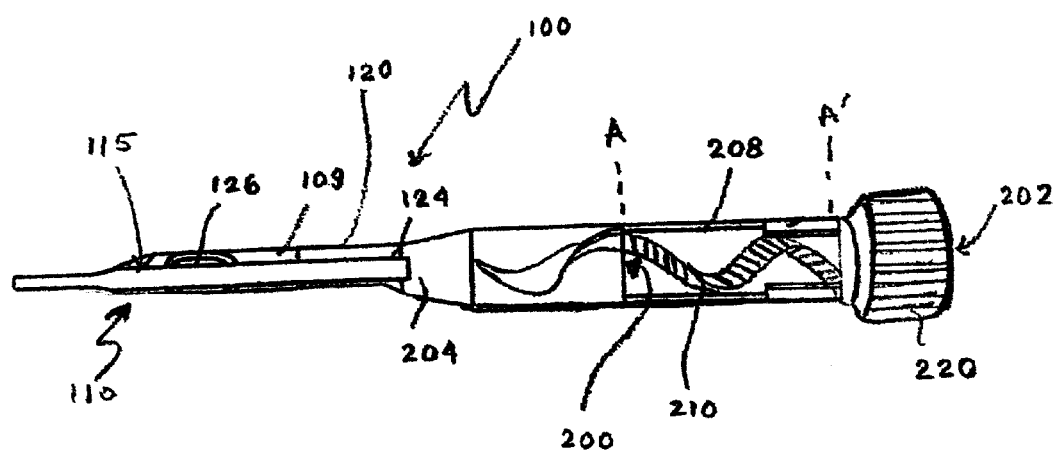
FIG. 3 is a side view of the assembly embodiment shown in FIGS. 1 and 2 with cross-section A–A'.

Among those benefits and improvements that have been disclosed, other objects and advantages of this invention will become apparent from the following description taken in conjunction with the accompanying drawings. The drawings constitute a part of this specification and include exemplary embodiments of the present invention and illustrate various objects and features thereof.

DETAILED DESCRIPTION OF THE INVENTION

As required, detailed embodiments of the present invention are disclosed herein;

however, it is to be understood that the disclosed embodiments are merely exemplary of the invention that may be embodied in various forms. The figures are not necessary to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

Referring now to FIGS. 1–4, one embodiment of the present invention relates to a dental tray and mixing tip assembly 100 having a rapid flow delivery device 120. The tray 110 comprises a material retention surface 115. The delivery device 20 comprises a channel 122 having an inlet 124 and an outlet 126, wherein the material is transferred from the inlet 124 through the channel 122 and out of the outlet 126 and onto the retention surface 115. The channel 122 and the retention surface 15 are situated on a horizontal plane. In this embodiment of the invention, the channel 122 is parallel to the retention surface 115. The outlet 126 of the channel 122 is situated parallel to the retention surface 115. The circumference of the channel 122a adjacent to the inlet 124 is greater than the circumference of the channel 122b adjacent to the outlet 126.

Figure 4:
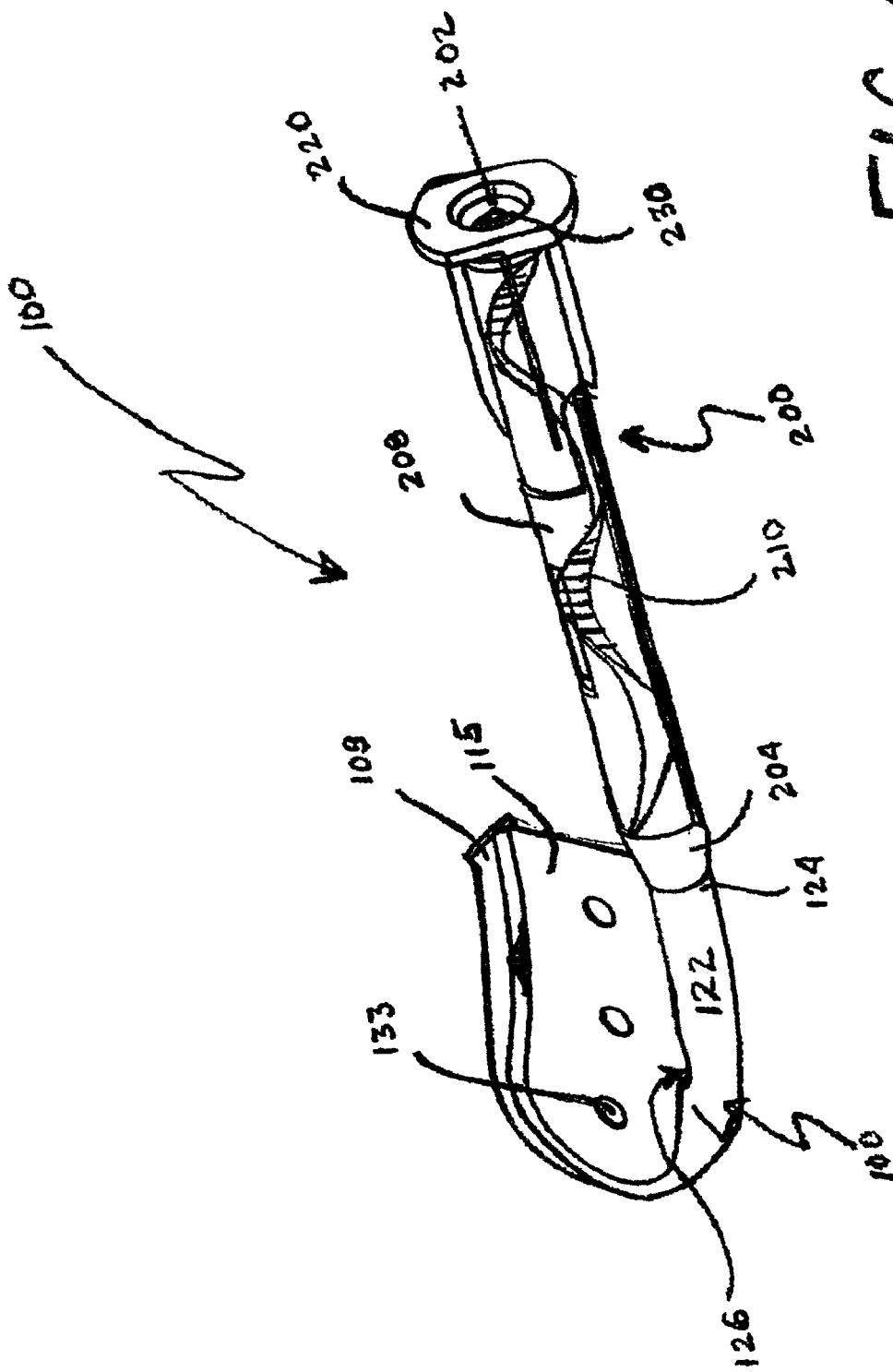
FIG. 4 is a perspective view of one of the embodiments of the present invention, in particular, an assembly wherein the mixing tip is parallel and on the same plane as the delivery device of the dental tray.

The assembly 100 comprises a mixing tip 200, which has an entrance 202 and exit 204. The mixing tip further comprises a mixing tube 208 and a mixing device, such as a twisted ribbon 210 as shown in cross-section A–A' in FIG. 3. The exit 204 of the mixing tip 200 is connected to the inlet 124 of the delivery device 120 of the dental tray 120. The tip 200 also comprises an adaptor or connector 220 for attaching the assembly onto a dispenser or gun (not shown). The adaptor 220 is situated near the entrance 202 of the mixing tip 200. There are at least two separate fluids that are enter the entrance 202 of the mixing tip 200 and are then mixed within the mixing tube 208 by the mixing device 210. The mixed fluid then leave the exit 204 of the mixing tip 200 and enters the inlet 124 of the tray 120 and travels through the channel 122 and then leaves the outlet 126 and then ends up in the retention surface 115. At this point the assembly is removed from the dispenser and is ready to be place in a patient's mouth to obtain an impression or registration of the teeth and the bite marks. In one embodiment, the mixing tip has a means 230 for preventing back flow of the fluids as shown in FIG. 4.

The tray also has peripheral walls 109 surrounding the retention surface 115. The peripheral walls 109 define the retention surface 115, and the delivery device 120 is incorporated within the peripheral walls 109. The tray 100 further comprises a plurality of apertures 133 situated within the retention surface 115.

Figure 5:
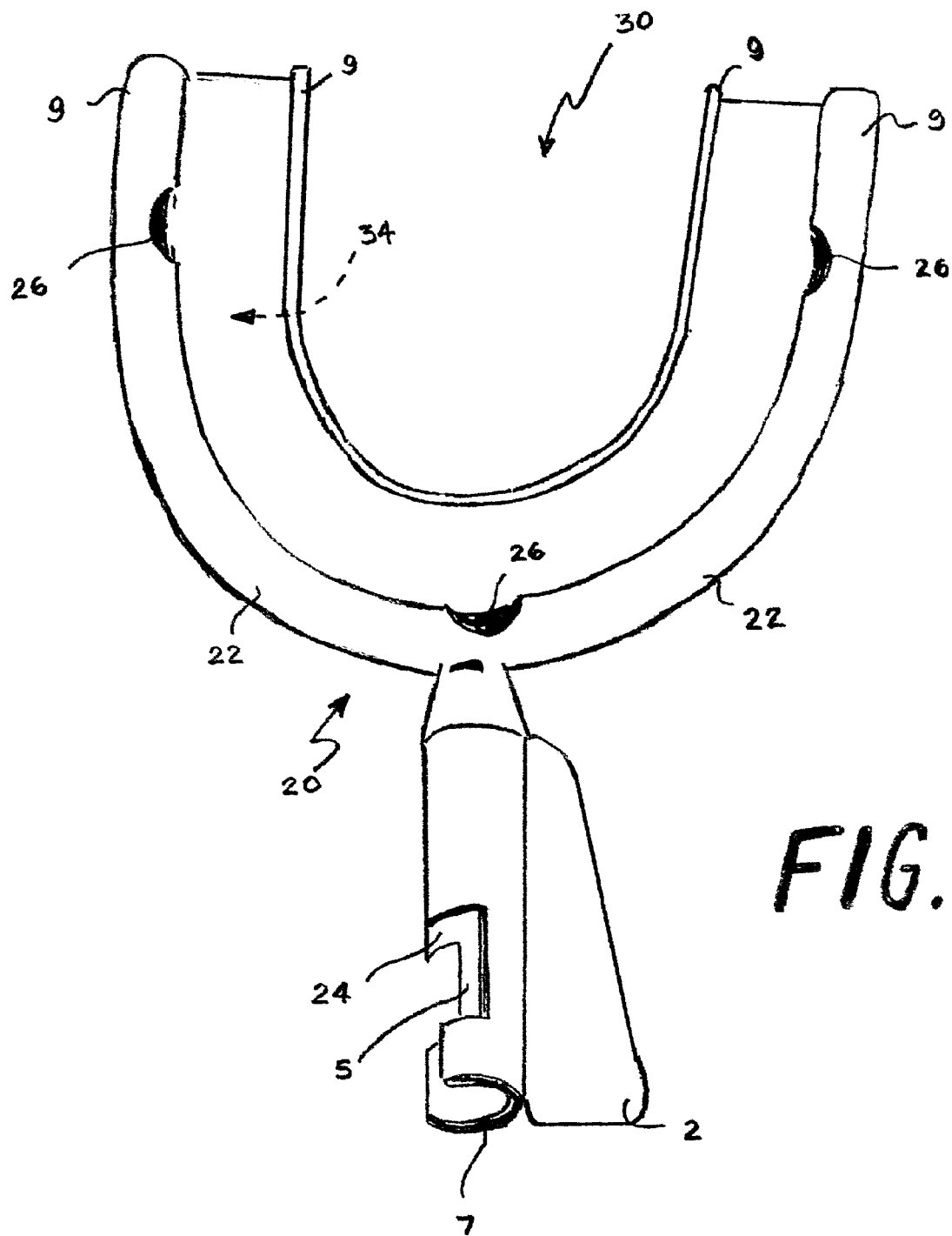
FIG. 5 is a perspective view of another embodiment of the present invention, in particular, a full arch triple tray mouthpiece.

FIG. 5 depicts a full arch triple tray mouthpiece 30 having the rapid flow delivery device 20. The mouthpiece 30 has an upper and lower portion 31 and 32 respectively. The upper portion 31 has an upper material retention surface 33 and the lower portion 32 has a lower material retention surface 34. The delivery device 20 has a channel 22 and at least one inlet 24 and at least one outlet 26. The channel 22 and the mouthpiece 30 are situated on a horizontal plane. The channel 22 is designed to deliver material from the inlet 24 through the channel 22 and out of the outlet 26 and onto the upper and lower retention surfaces, 33 and 34 respectively.

The mouthpiece 30 further comprises an ergonomically designed handle 2. In this embodiment, the handle 2 is connected to the delivery device 20. The inlet 24 further comprises a mixing tube sleeve 5 and a snap clip 7 for holding and retaining a mixing tube (not shown).

The mouthpiece 30 also has peripheral walls 9 surrounding the retention surfaces 33 and 34. The peripheral walls 9 define the retention surfaces 33 and 34, and the delivery device 20 is incorporated within the peripheral walls 9.

Figure 6:
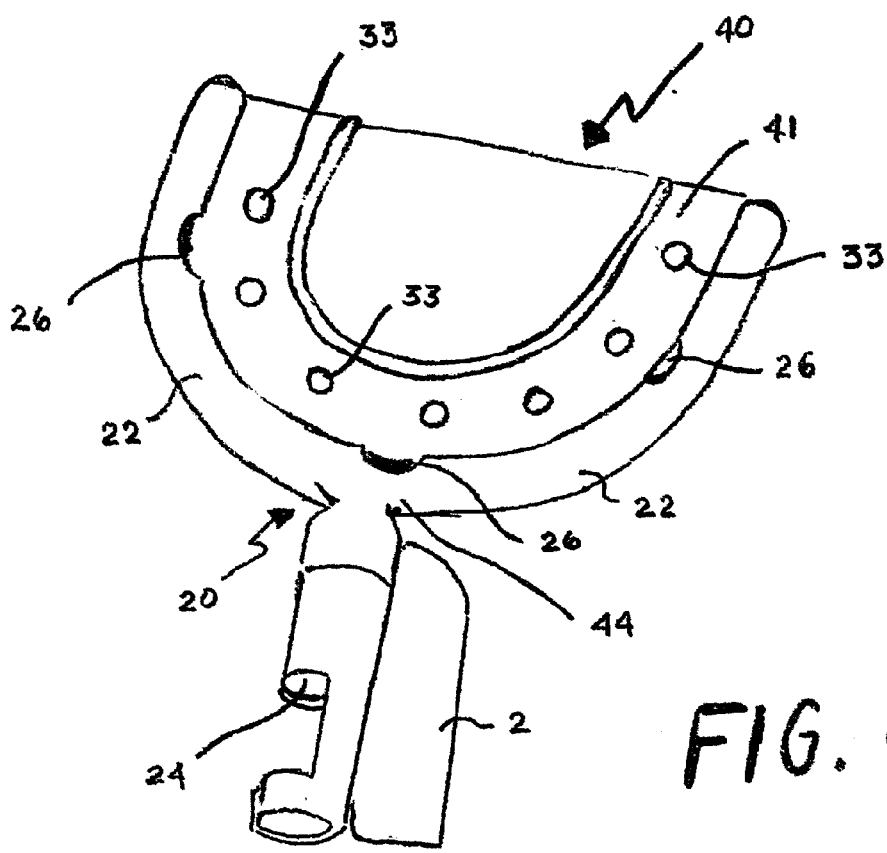
FIG. 6 is a perspective view of another embodiment of the rapid flow delivery device of the present invention in use with an anterior single tray.
Figure 7:
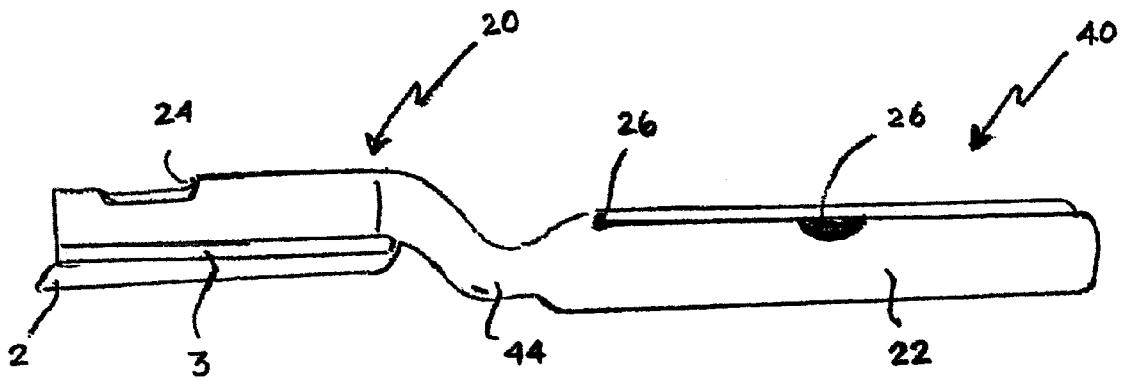
FIG. 7 is a side view of the impression tray in FIG. 6.

FIGS. 6–7 illustrates another embodiment of the rapid flow delivery device 20 of the present invention in use with an anterior single tray 40. The tray 40 has a material retention surface 41. The delivery device 20 comprises a channel 22 with an inlet 24 and a plurality of outlets 26. In this embodiment, a portion of the channel 22 is positioned above the retention surface 41; the channel 22 being designed to deliver material from the inlet 24 through the outlets 26 and onto the retention surface 41. In this embodiment, the outlets 26 of the channel 22 are positioned above the retention surface 41 using gravity in the delivery of the material. The tray 40 further comprises a connector 44 situated between the channel 22 and the delivery device 20. The connector 44 is an elbow connection. The retention surface 41 of the tray 40 further comprises a plurality of apertures 33. FIG. 8 depicts a quadrant triple tray 50 having the rapid flow delivery device 20 of the present invention.

The tray and delivery device of the present invention is used in the following manner: (1) place the mixing tube or tip 1 within the mixing tube sleeve 5 and a snap clip 7 of the tray 10; (2) the handle 2 should be held in an upright 12 o'clock position thereby allowing the outlet 26 to be facing downward; (3) the impression gun is then squeezed with moderate and even pressure to begin mixing the impression material within the mixing tube 1 (use a generous and even amount of impression material) and then release the trigger of the gun to cease flow of the impression material; (5) once the material fills the retention surfaces 15 and 16; and (6) remove the tray 10 from the mixing tube 1 and the tray 10 is loaded and ready to take an impression.

Numerous modifications and variations of the present invention are possible in light of the above teachings. It is therefore to be understood that within the scope of the attendant claims attached hereto, this invention may be practiced otherwise than as specifically disclosed herein.

What is claimed is:

1. A dental tray comprising:
   at least one material retention surface and peripheral walls surrounding at least a portion of said retention surface; and
   a rapid flow delivery device, said device comprising a channel having an inlet and at least one outlet, said channel and said retention surface being situated on a horizontal plane, said channel being designed to deliver material from said inlet through said outlet and onto said retention surface, said delivery device being incorporated within said peripheral walls, a portion of said delivery device extending along a portion of said peripheral walls.

2. The tray of claim 1 wherein said channel is parallel to said retention surface.

3. The tray of claim 1 wherein said outlet of said channel is parallel to said retention surface.

4. The tray of claim 1 further comprises a handle, said handle being connected to said delivery device.

5. The tray of claim 1 wherein the circumference of said channel adjacent to said inlet being greater than the circumference of said channel adjacent to said outlet.

6. A dental tray and mixing tip assembly comprising:

a tray comprising at least one material retention surface and peripheral walls surrounding at least a portion of said retention surface; and a rapid flow delivery device, said device comprising a channel having an inlet and at least one outlet, a portion of said channel being positioned above said retention surface, said channel being designed to deliver material from said inlet through said outlet and onto said retention surface, said delivery device being incorporated within said peripheral walls; and a mixing tip comprising a mixing tube having an entrance and an exit; a mixing device situated within said tube, and said exit of said tip being connected to said inlet of said channel of said delivery device of said tray.

7. The assembly of claim 6 wherein said channel is parallel to said retention surface.

8. The assembly of claim 6 wherein said outlet of said channel is parallel to said retention surface.

9. The assembly of claim 6 further comprises a connector situated between said channel and said delivery device.

10. The assembly of claim 9 wherein said connector is an elbow connection.

11. The assembly of claim 6 wherein the circumference of said channel adjacent to said inlet being greater than the circumference of said channel adjacent to said outlet.

12. The assembly of claim 6 wherein said mixing device is rotatable within said mixing tube, whereby a pressure created by the flow of at least two separate fluids entering said entrance of said tube causes said mixing device to rotate and thereby mix the fluids.

13. The assembly of claim 12 wherein said mixing device comprises twisted ribbon.

14. The assembly of claim 12 wherein said tip further comprises a means for preventing the back flow of the fluids to be mixed and thereby preventing the fluids from exiting said entrance of said tip.

15. A dental tray and mixing tip assembly comprising:

a mouthpiece having an upper and lower portion, said upper portion having an upper material retention surface, said lower portion having a lower material retention surface and said mouthpiece further comprising peripheral walls; and a rapid flow delivery device, said device comprising a channel having an inlet and at least one outlet, said channel being situated on a horizontal plane with said upper retention surface and being situated above said lower retention surface, said channel being designed to deliver material from said inlet through said outlet and onto both said upper and lower retention surfaces, said channel being situated within said peripheral walls of said mouthpiece; and a mixing tip for receiving and mixing at least two separate fluids, said tip comprising a mixing tube having an entrance and an exit; a means for mixing the fluids, said mixing means being situated within said tube, and said exit of said tip being connected to said delivery device of said tray.

16. The assembly of claim 15 wherein said mixing device is moveable within said mixing tube, whereby a pressure created by the flow of at least two separate fluids entering said entrance of said tube causes said mixing device to move and thereby mix the fluids.

17. The assembly of claim 15 wherein said mixing device comprises twisted ribbon.

18. The assembly of claim 15 wherein said tip further comprises a means for preventing the back flow of the fluids to be mixed and thereby preventing the fluids from exiting said entrance of said tip.

* * * * *